(12) United States Patent
Ptchelintsev et al.

(10) Patent No.: US 8,168,212 B2
(45) Date of Patent: May 1, 2012

(54) TOPICAL COMPOSITIONS COMPRISING NON-PROTEOGENIC AMINO ACIDS AND METHODS OF TREATING SKIN

(75) Inventors: Dmitri S. Ptchelintsev, Jersey City, NJ (US); Laurence Dryer, Long Beach, CA (US); Xiaochun Luo, New City, NY (US)

(73) Assignee: Avon Products, Inc, New York, NY (US)

(*) Notice: Subject to any disclaimer, the term of this patent is extended or adjusted under 35 U.S.C. 154(b) by 0 days.

(21) Appl. No.: 12/747,272

(22) PCT Filed: Nov. 14, 2008

(86) PCT No.: PCT/US2008/083490
§ 371 (c)(1),
(2), (4) Date: Jun. 10, 2010

(87) PCT Pub. No.: WO2009/079126
PCT Pub. Date: Jun. 25, 2009

(65) Prior Publication Data
US 2010/0261769 A1    Oct. 14, 2010

Related U.S. Application Data

(60) Provisional application No. 61/014,846, filed on Dec. 19, 2007.

(51) Int. Cl.
*A61K 8/02*     (2006.01)
*A61K 31/385*   (2006.01)
*A01N 43/26*    (2006.01)

(52) U.S. Cl. ..................................... 424/401; 514/439
(58) Field of Classification Search .................. 424/401; 514/439
See application file for complete search history.

(56) References Cited

U.S. PATENT DOCUMENTS

| | | | |
|---|---|---|---|
| 5,122,514 A | 6/1992 | Boger et al. | |
| 5,508,295 A | 4/1996 | Hanson et al. | |
| 5,851,994 A | 12/1998 | Schreiber et al. | |
| 6,267,978 B1 * | 7/2001 | Sang et al. | 424/401 |
| 2005/0188427 A1 | 8/2005 | Li et al. | |

FOREIGN PATENT DOCUMENTS
WO    2007/056464 A1    5/2007

OTHER PUBLICATIONS

Jones et al (J. Am. Chem. Soc., 1950, 72 (10), pp. 4526-4529).*
Noblesse et al., "Lysyl Oxidase-Like and Lysyl Oxidase are present in the Dermis and Epidermis...", J. Invest Dermatol., Mar. 2004; 122 (3):621-30.
Kiety et al., Elastic fibres; J. Cell Sci., Jul. 15, 2002; 115 (Pt 14):2817-28.

(Continued)

Primary Examiner — Benjamin Packard
(74) Attorney, Agent, or Firm — Charles J. Zeller; Joan M. McGillycuddy; David M. Jogal (57) ABSTRACT

Cosmetic compositions comprising non-natural, non-proteogenic amino acids and methods of using such compositions to impart antiaging benefits to the skin are disclosed.
The non-natural, non-proteogenic amino acids are believed to have modulatory activity against one or more biochemical pathways implicated in skin aging, and in particular, are enhancers of LOXL-1.

11 Claims, 4 Drawing Sheets

L-4-Thiazolylalanine

D-4-Thiazolylalanine

L-2-Thiazolylalanine

D-2-Thiazolylalanine

L-2-Thienylalanine

D-2-Thienylalanine

L-3-Thienylalanine

D-3-Thienylalanine

L-2-Furylalanine

D-2-Furylalanine

L-2-Pyridylalanine

D-2-Pyridylalanine

OTHER PUBLICATIONS

Lucero et al.; Lysyl oxidase: an oxidative enzyme and effector of cell function; Cell Mol. Life Sci., Oct. 2006; 63 (19-20):2304-16.

Liu et al., Elastic fiber homeostasis requires lysyl oxidase—like 1 protein; Nat. Genet, Feb. 2004;36(2):178-82.

Genizo et al.; LOXL as a target to increase the elastin content in adult skin: a dill extract induces the LOXL gene expression; Exp. Dermatol., Aug. 2006; 15 (8):574-81.

* cited by examiner

L-4-Thiazolylalanine

D-4-Thiazolylalanine

L-2-Thiazolylalanine

D-2-Thiazolylalanine

L-2-Thienylalanine

D-2-Thienylalanine

L-3-Thienylalanine

D-3-Thienylalanine

L-2-Furylalanine

D-2-Furylalanine

L-2-Pyridylalanine

D-2-Pyridylalanine

FIGURE 1

L-3-Pyridylalanine

D-3-Pyridylalanine

L-4-Pyridylalanine

D-4-Pyridylalanine

L-beta-homotryptophan

D-beta-homotryptophan

L-beta-homohistidine

D-beta-homohistidine

D-histidine

L-2-Thienylglycine

D-2-Thienylglycine

D-Ala-3-(2-N-tetrazoyl)

FIGURE 1 (Cont.)

L-Ala-3-(2-N-tetrazoyl)  L-Ala-3-(5-N-tetrazoyl)  D-Ala-3-(5-N-tetrazoyl)

L-3-Benzothienylalanine  D-3-Benzothienylalanine  L-Ala-[3-(3-pyrazoyl)]

D-Ala-[3-(3-pyrazoyl)]  L-Ala-[3-(4-pyrimidinyl)]  D-Ala-[3-(4-pyrimidinyl)]

L-Ala-3-[5-(2-amino)thiazoyl]  D-Ala-3-[5-(2-amino)thiazoyl]  (2S)-Gly-3-[5-(2-N-amino)thiazoyl]

FIGURE 1 (Cont.)

(2R)-Gly-3-[5-(2-amino)thiazoyl]

3-L- pyrroylglycine

3-D- pyrroylglycine

3-L- pyrroylalanine

3-D- pyrroylalanine

D-His(2-NH$_2$)

L-His(2-NH$_2$)

FIGURE 1 (Cont.)

TOPICAL COMPOSITIONS COMPRISING NON-PROTEOGENIC AMINO ACIDS AND METHODS OF TREATING SKIN

RELATED APPLICATIONS

This application claims priority to International Application Serial No. PCT/US08/83490 filed Nov. 14, 2008, which claims priority U.S. Provisional Patent Application Ser. No. 61/014,846, filed Dec. 17, 2007, the contents of which are hereby incorporated by reference in their entirety.

FIELD OF INVENTION

The present invention relates generally to compositions for topical application to the skin which comprise non-proteogenic amino acids and the use of such compositions to provide benefits to the skin.

BACKGROUND OF THE INVENTION

Elastic fibers are essential extracellular matrix macromolecules comprising an elastin core surrounded by a mantle of fibrillin-rich microfibrils (Kiety et al., *J. Cell Sci.,* 2002 Jul. 15; 115 (Pt 14):2817-28). Elastic fibers provide elasticity and resilience to tissues such as skin and lung. Production of a mature and functional elastic fiber is a complex process because it involves multiple components and requires a tightly regulated deposition and a multi-step hierarchical assembly. Monomers of elastin (tropoelastin) are cross-linked in the extracellular space by one or more members of the lysyl oxidase family to form an elastin polymer, which is the functional form of the mature protein. Fibrillin-containing microfibrils are thought to play an important role in the assembly process by serving as a scaffold for aligning cross-linking domains within tropoelastin.

Lysyl oxidase like-1 (LOXL1) is a member of the lysyl oxidase family which catalyzes the cross-linking of collagen and elastin through oxidative deamination of lysine or hydroxylysine side chains. The resultant allysine residues can spontaneously condense with vicinal peptide aldehydes or with $\epsilon$-amino groups of peptidyl lysine to generate covalent cross-linkages (Lucero et al., *Cell Mol. Life. Sci.,* 2006 October; 63 (19-20):2304-16). LOXL1 is an extracellular enzyme associated with elastin fibers (Noblesse et al., *J. Invest. Dermatol.,* 2004 March; 122 (3):621-30.). LOXL1 is expressed in the epidermis and dermis of a skin equivalent and in human skin LOXL1 is essential for elastic fiber formation and maintenance of elastic fibers homeostasis. LOXL1 knock-out mice have a connective tissue phenotype characterized by pelvic laxity in female animals and enlarged pulmonary air spaces that result from decreased elastin content (Liu et al., *Nat. Genet.,* 2004 February; 36(2):178-82). Ultrastructural analysis shows poorly developed, fragmented and discontinuous elastic fibers in lung and skin In addition, mice lacking LOXL1 do not deposit normal elastic fibers in the postpartum uterus and develop loose skin and vascular abnormality with concomitant tropoelastin accumulation. Recent studies indicate that the LOXL1 mRNA level is reduced in adult skin fibroblasts compared with fibroblasts from children (Genizo et al., *Exp. Dermatol.,* 2006 August; 15 (8):574-81.).

U.S. Patent Pub. No. 2005/0188427, the disclosure of which is hereby incorporated by reference, discloses a method of treating a subject having a condition associated with a loss of elastic fibers, such as loose or wrinkly skin, comprising administering to the subject a therapeutically effective amount of a LOXL1 enhancer. The LOXL1 enhancers are said to be LOXL1 polypeptides or active fragments thereof, or a nucleic acid encoding a LOXL1 polypeptide or active fragment thereof. The LOXL1 enhancers are also said to include small molecules or other therapeutic compounds identified by the screening method disclosed in that publication. There is no disclosure in U.S. Patent Pub. No. 2005/0188427 of the use of amino acids, other than in peptide form, to enhance LOXL1 expression.

Amino acids have become increasingly important constituents of cosmetics. For example, various natural amino acids have been incorporated into cosmetics as building blocks for collagen and elastin synthesis, for moisture retention, enhancing the skin barrier, reduction in sebaceous gland activity, and other functional properties. However, the use of non-natural, non-proteogenic amino acids has received little attention in the cosmetic industry. To date, the use of non-natural amino acids has been limited, for the most part, to imparting hydrolytic stability to functional peptides. Non-proteogenic aminoacids, by definition, do not become incorporated into proteins during new protein synthesis, and therefore, it would not be predicted that topical application of non-proteogenic aminoacids would lead to new protein synthesis in the skin and to skin rejuvenation benefits. The intrinsic functionality of non-natural, non-proteogenic amino acids has been largely ignored. The ability of non-natural, non-proteogenic amino acids to enhance LOXL-1 and modulate other pathways implicated in skin aging is heretofore unknown.

It is therefore an object of the invention to provide new cosmetic compositions and methods for enhancing LOXL-1 production in the skin using non-natural, non-proteogenic amino acids. It is a further object of the invention to provide cosmetic compositions and methods for improving the appearance of skin, including treating, reversing, and/or preventing signs of aging, such as skin wrinkles, using non-natural, non-proteogenic amino acids.

The foregoing discussion is presented solely to provide a better understanding of nature of the problems confronting the art and should not be construed in any way as an admission as to prior art nor should the citation of any reference herein be construed as an admission that such reference constitutes "prior art" to the instant application.

SUMMARY OF THE INVENTION

In accordance with the foregoing objectives and others, it has surprisingly been found that certain non-proteogenic amino acids are potent stimulators of LOXL-1 and thus are expected to provide numerous skin benefits owing to the ability of LOXL-1 to remodel and maintain the elastin fibers in skin. In addition to LOXL-1 stimulation, the non-proteogenic aminoacids are expected to play a beneficial role in one or more additional biological pathways implicated in skin aging, as discussed more fully herein, although such additional benefits are not strictly required.

In one aspect of the invention, cosmetic compositions are provided for treating a skin condition associated with loss of elastin fiber comprising an effective amount of a LOXL-1 enhancing non-proteogenic aminoacid or derivative thereof in a cosmetically acceptable vehicle. In preferred embodiments, the non-proteogenic amino acids will comprise a side chain having a heterocyclic, preferably heteroaromatic, group. The preferred amino acids will comprise a nitrogen-containing heterocyclic or heteroaromatic ring. The currently preferred non-proteogenic amino acid according to the invention is L-4-thiazolylalanine, having the structure:

In another aspect, cosmetic compositions are provided comprising, in a cosmetically acceptable vehicle, an amount of thiazolylalanine or a derivative thereof effective to enhance LOXL-1 in the skin. The thiazolylalanine is typically L-thiazolylalanine or a derivative thereof, preferably, L-4-thiazolylalanine or a derivative thereof.

Also provided is a method of treating a skin condition associated with loss of elastin fibers in the skin, comprising topically applying to skin in need thereof a LOXL-1 enhancing non-proteogenic aminoacid or derivative thereof, in an amount effective to enhance LOXL-1. The non-proteogenic aminoacid may further be capable of one or more additional activities selected from the group consisting of inhibiting calcineurin, increasing expression of β1 integrin, increasing expression of fibronectin, stimulation of B-endorphin, and increasing expression of CGRP.

In another aspect of the invention, a method of treating, ameliorating, and/or preventing fine lines or wrinkles or sagging in human skin is provided, comprising topically applying to skin in need thereof a composition comprising a LOXL-1 enhancing non-proteogenic amino acid. In specific embodiments, the non-proteogenic amino acid is thiazolylalanine or a derivative thereof, more typically L-thiazolylalanine or a derivative thereof, and preferably, L-4-thiazolylalanine or a derivative thereof. Thus, the preferred method of treating fine lines or wrinkles according to this aspect of the invention comprises topically applying to a fine line or wrinkle a composition comprising L-4-thiazolylalanine.

These and other aspects of the present invention will be better understood by reference to the following detailed description and accompanying FIGURES.

DETAILED DESCRIPTION

Figure 1:
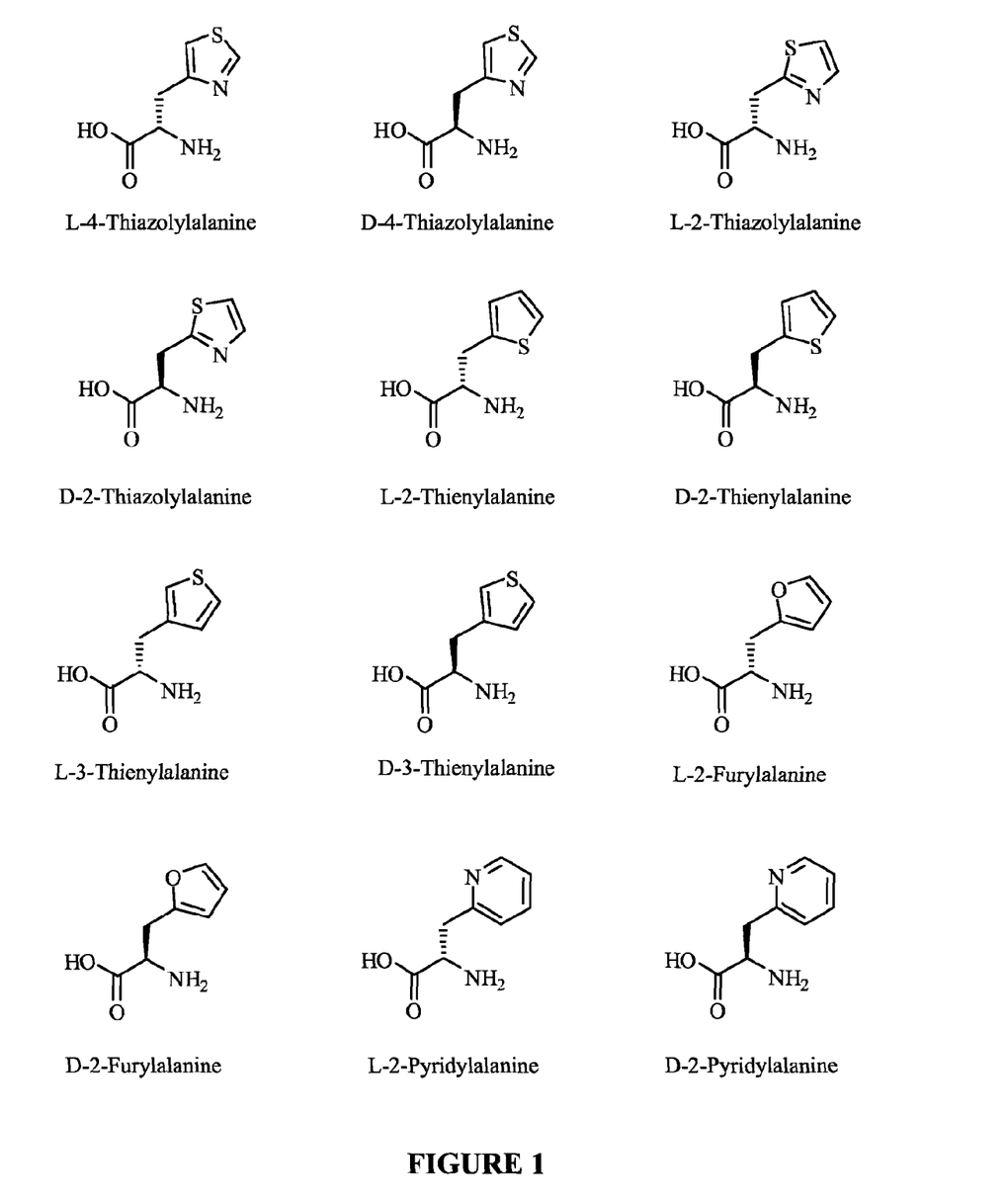
FIG. 1 illustrates various non-proteogenic amino acids according to the invention. The amino acids shown in FIG. 1 are merely illustrative and not intended to be limiting.

All terms used herein are intended to have their ordinary meaning unless otherwise provided.

The term "amino acid" refers generally to an organic molecule which contains an amino group and a carboxyl group in the same molecule. The term "α-amino acid" refers to an amino acid in which the amino group and carboxyl group are attached to the same carbon atom. The term "β-amino acid" refers to an amino acid in which the amino group and carboxyl group are attached to adjacent carbon atoms.

"Natural amino acid" refers to any amino acid synthesized by an organism in nature, including without limitation, the standard amino acids L-alanine, L-valine, L-leucine, L-isoleucine, L-proline, L-tryptophan, L-phenylalanine, L-methionine, glycine, L-serine, L-tyrosine, L-threonine, L-cysteine, L-cystine, L-asparagine, L-glutamine, L-aspartic acid, L-glutamic acid, L-lysine, L-arginine, L-histidine, and other non-standard amino acids, such as L-ornithine, and derivatives, such as L-4-hydroxyproline.

"Non-natural amino acid" refers broadly to any amino acid other than a "natural amino acid," and includes, without limitation, α-amino acids having side chains not found in natural amino acids, as well as β-amino acids. "Non-natural amino acids" also refers to amino acids having the same structure as natural amino acids, albeit in a different stereochemical configuration.

"Non-proteogenic" amino acid broadly refers to any amino acid which is not capable of being incorporated into peptides or proteins by a living organism and includes non-natural amino acids.

The present invention provides compositions for topical application which comprise an effective amount of one or more non-proteogenic amino acids to treat, reverse, ameliorate and/or prevent signs of skin aging. Such signs of skin aging include without limitation, the following:

(a) treatment, reduction, and/or prevention of fine lines or wrinkles,
(b) reduction of skin pore size,
(c) improvement in skin thickness, plumpness, and/or tautness;
(d) improvement in skin suppleness and/or softness;
(e) improvement in skin tone, radiance, and/or clarity;
(f) improvement in procollagen and/or collagen production;
(g) improvement in maintenance and remodeling of elastin;
(h) improvement in skin texture and/or promotion of retexturization;
(i) improvement in skin barrier repair and/or function;
(j) improvement in appearance of skin contours;
(k) restoration of skin luster and/or brightness;
(l) replenishment of essential nutrients and/or constituents in the skin;
(m) decreased by aging and/or menopause;
(n) improvement in skin moisturization; and/or
(o) increase in skin elasticity and/or resiliency.

In practice, the compositions of the invention are applied to skin in need of treatment. That is, skin which suffers from a deficiency or loss in any of the foregoing attributes or which would otherwise benefit from improvement in any of the foregoing skin attributes.

In certain preferred embodiments the compositions and methods of the invention are directed to the prevention, treatment, and/or amelioration of fine lines and/or wrinkles in the skin. In this case, the compositions are applied to skin in need of treatment, by which is meant skin having wrinkles and/or fine lines. Preferably, the compositions are applied directly to the fine lines and/or wrinkles. The compositions and methods are suitable for treating fine lines and/or wrinkles on any surface of the skin, including without limitation, the skin of the face, neck, and/or hands.

Generally, the compositions and methods are useful for treating any skin condition associate with loss of elastic fibers. These benefits are believed to arise, at least in part, from the ability of the compounds to stimulate production of LOXL-1. In other words, the non-proteogenic amino acids of the invention are LOXL-1 enhancers.

The amino acids according to the invention are in "free" or monomeric form, by which is meant that they are not covalently bound to other amino acids, but otherwise may be functionalized as pro-drugs and the like as described herein.

The amino acids useful in the practice of this invention may be any non-proteogenic amino acids which reduce, treat, or prevent one or more signs of aging. Typically, the non-proteogenic amino acids of the invention will be capable of stimulating LOXL-1. In one embodiment, the non-proteogenic amino acid will have the structure of formula I:

where n is an integer from 0 (zero) to 4, typically from 0 to 2, and preferably will be either 0 or 1, such that in the case where n is 0, the amino acid is an α-amino acid and in the case where n is 1, the amino acid is a β-amino acid;

R is a side chain comprising any organic substitutent, with the proviso that where n is 0 (i.e., an α-amino acid), the side chain is not a side chain present in the proteogenic, naturally occurring amino acids in the case where the amino acid of formula I is in the L (levorotary) configuration;

R is typically a hydrocarbon radical comprising from 1-20 carbon atoms and optionally including one or more heteroatoms, such as oxygen, sulfur, and nitrogen atoms. Preferably, R is selected from substituted or unsubstituted branched, straight chain or cyclic $C_1$-$C_{20}$ alkyl, alkenyl, alkynyl, aryl, benzyl, heteroaryl, alkyl-aryl, aryl-alkyl, alkyl-heteroaryl, heteroaryl-alkyl, heteroaryl-aryl, bicyclic alkyl, aryl, or heteroaryl radicals, and combinations thereof; wherein the foregoing radicals may be substituted with any moiety, including, for example, hydroxyl, amino, cyano, halogen, oxo, carboxy, carboxamide, nitro, azo, alkoxyl, alkyl, alkylimino, alkylamino, dialkylamino, thioalkoxy and combinations thereof.

In preferred embodiments, R will comprise a heterocyclic ring. The heterocyclic ring may be either monocyclic or bicyclic and may be aromatic, partially saturated, or fully saturated. Preferred heterocyclic rings will comprise a nitrogen atom. Representative heterocyclic rings include, without limitation, azetidinyl, benzimidazolyl, benzothiazolyl, benzothienyl, benzoxazolyl, furyl, imidazolyl, imidazolinyl, isoquinolinyl, isoxazolyl, isoxazolidinyl, isothiazolyl, isothiazolidinyl, indolyl, oxazolyl, oxazolidinyl, pyrryl, pyrrolinyl, pyrrolidinyl, pyrazolyl, pyrazolinyl, pyrazolidinyl, pyridyl, piperidinyl, pyrazinyl, piperazinyl, N-methylpiperazinyl, N-methylazetidinyl, pyrimidinyl, pyridazinyl, morpholinyl, quinolinyl, thiazolyl, thiazolidinyl, thienyl, triazolyl and the like.

The dotted line is intended to indicate that R may be a divalent radical which forms a ring with the nitrogen atom, as in the case of proline and hyrdoxyproline analogs, for example, although such structures are less preferred.

In one embodiment, the amino acid is an α-amino acid or a β-amino acid comprising a heterocyclic group according to formula Ia:

where n is either 0 (α-amino acid) or 1 (β-amino acid);

Z may represent a bond (i.e., Z is omitted) or Z may represent a linker moiety attached at the α-carbon which is in turn attached to a heterocyclic ring Q through substituent Y; wherein Z typically comprises from 1 to 10 carbon atoms, optionally including one or more heteroatom substituents such as oxygen, sulfur, and nitrogen. Typically, Z will be selected from the group consisting of oxygen, sulfur, $NR^N$, $C_{1-10}$ alkyl, alkenyl, alkynyl, aryl, carbonyl, carboxyl, carbamyl, where $R^N$ is hydrogen, $C_{1-10}$ alkyl, alkenyl, alkynyl, aryl, or the like.

Z is preferably a bond or a moiety selected from the group consisting of substituted or unsubstituted branched or straight chain $C_{1-6}$ alkyl, alkenyl, alkynyl, aryl, heteroaryl, or alkylaryl groups, including without limitation, linear alkyl moieties of the form —$(CH_2)_a$— where "a" is an integer from 1 to 6, including, for example, —$CH_2$— (methylene), —$CH_2CH_2$—, —$CH_2CH_2CH_2$—, or —$CH_2CH_2CH_2CH_2$—; linear alkoxy moieties of the general form —$(CH_2)_aO$— or —$O(CH_2)_a$— where "a" is an integer from 1 to 6, including for example, —$CH_2O$— or —$OCH_2$—, —$CH_2CH_2O$— or —$OCH_2CH_2$—, —$CH_2CH_2CH_2O$— or —$OCH_2CH_2CH_2$—; —$O(CH_2)_aO$— where "a" is as defined above; or a moiety of the form —$(CH_2)_bO(CH_2)_c$—, —$(CH_2)_b$ $S(CH_2)_c$—, or —$(CH_2)_bNR^N(CH_2)_c$— wherein "b" and "c" are independently an integer from 0 (zero) to 6 and $R^N$ is as defined above. Preferably, Z represents a single bond between Y and the α-carbon or Z is a group —$CH_2$— or —$CH_2CH_2$—, —$CH_2O$—, —$CH_2S$—, —$CH_2NR^N$, — or —(C=O)—. In one exemplary embodiment, Z is (—$CH_2$—)$_{1-3}$ and is more preferably —$CH_2$—;

Y is the point of attachment of ring Q to linker or bond Z and is typically a carbon or a heteroatom, and is more typically selected from C, CH, N, or $NR^N$, where $R^N$ is as defined above; and Q is a 3-14 membered heterocyclic group which includes Y and may be monocyclic, bicyclic, or tricyclic, including fused ring systems, and which comprises one or more heteroatoms in the ring system, typically selected from oxygen, nitrogen, and sulfur, and is optionally substituted with one or more groups $R_1$ attached to the ring system at any suitable point of attachment (e.g., on any carbon or nitrogen atom), wherein $R_1$ is independently, at each occurrence, selected from hydrogen, halogen (F, Cl, Br, I); —OH; —$NR^NR^N$; —SH; —CN; oxo; —CHO; —$CO_2H$; —O—(C=O)—H; —O—(C=O)—$C_{1-10}$ alkyl; —O—(C=O)—Ar; —(C=O)—O—$C_{1-10}$ alkyl; —(C=O)—O—Ar; —(C=O)—$NR^NR^N$; —O—$C_{1-10}$ alkyl; —O—Ar; —S—$C_{1-10}$ alkyl; —S-aryl; —Ar; —$C_{1-10}$ alkyl; —$NR^N$—CHO; —$NR^N$—(C=O)—$C_{1-10}$ alkyl; —$C_{1-10}$alkyl-O—$C_{1-10}$alkyl; perfluoroalkyl; epoxy; azido; thiocyanate; —$SO_2$—$R^N$; nitro, or the like; wherein Ar designates an optionally substituted aryl group, $R^N$ is as defined above and in the case where the substituent comprises two group $R^N$, they may together form a ring; with the proviso that when n=0 in the case of an α-amino acid, the compound of formula Ia is not L-histidine or L-tryptophan.

In some embodiments Q will comprise at least one heteroatom in addition to Y in the case where Y is also a heteroatom, the at least one additional heteroatom being selected from N, O, S, B, Si, As, P, and the like, but is more typically selected from N, O, and S.

Non-limiting examples of three-membered heterocyclic rings, include but are not limited to, aziridine, oxirane, thiirane, diaziridine, and oxaziridine. Non-limiting examples of four-membered heterocyclic rings, include but are not limited to, azetidine, oxetane, thietane, diazetidine, oxazetidine, and 1,2-oxathietane.

Five membered heterocycles represent the currently preferred embodiment of the invention for the substituent Q. Non-limiting examples of five-membered heterocyclic rings include, without limitation, pyrrolidine, tetrahydrofuran, tetrahydrothiophene, oxazolidine, thiazolidine, 1,3-dioiane, 1,3-oxzthiolane, 1,3-dithiolane, imidazolidine, pyrazolidine, pyrrole, furan, thiophene, oxazole, isoxazole, thiazole, isothiazole, imidazole, pyrazole, 1,3,4-oxadiazole, 1,2,4-oxadiazole, 1,3,4-thiadiazole, 1,2,4-thiadiazole, 1,3,4-triazole, 1,2,3-triazole, and the like. Q may be selected from, for example, the following five membered heterocyclic rings which are aromatic, fully saturated, or comprises one, or two double bonds:

-continued

In each of the foregoing five membered rings comprising the ring substituents O and/or S, it will be understood that the point of attachment to the ring is other than a sulfur or oxygen atom, by which is meant that Y is either C, CH, or N, rather than O or S. These five membered rings may be optionally functionalized with one or more groups $R_1$, as defined above, with particular mention being made of halo, hydroxyl, oxo, thiol, $C_{1-4}$ alkyl (e.g., methyl, ethyl, isopropyl, etc.), amino, and dialkylamino. Further, any nitrogen atom may be optionally oxidized to the N-oxide, and any sulfur atom may be optionally oxidized to a sulfoxide.

Non-limiting examples of six-membered rings which are suitably selected for Q include, without limitation, 2H-pyran, tetrahydropyran, piperidine, 1,4-dioxane, morpholine, piperazine, 1,4-dithiane, thiomorpholine, pyridine, pyrazine, pyridazine, pyrimidine, 1,2,3-triazine, 1,2,4-triazine, 1,3,5-triazine, 1,2,3,4-tetrazine, and pentazine, to name a few. Q may be selected from, for example, the following six membered heterocyclic rings which are aromatic, fully saturated, or comprises one, two, or three double bonds:

In each of the foregoing six membered rings comprising the ring substituents O and/or S, it will be understood that the point of attachment to the ring is other than a sulfur or oxygen atom, by which is meant that Y is either C, CH, or N, rather than O or S. These six membered rings may be optionally functionalized with one or more groups $R_1$, as defined above, with particular mention being made of halo, hydroxyl, oxo, thiol, $C_{1-4}$ alkyl (e.g., methyl, ethyl, isopropyl, etc.), amino, and dialkylamino. Further, any nitrogen atom may be optionally oxidized to the N-oxide, and any sulfur atom may be optionally oxidized to a sulfoxide.

Seven membered heterocycles include, without limitation, 1H-azepine, oxepin, thiepin, 1,4-diazepine, 1,3-dioxepin, 1,3-dithiepin, 1H-1,3,5-triazepine, 1,2-oxazepine, 1,3-thiazepine, 1,3,6-thiadiazepine, tetrazepine, 1,2,4,7-thiatriazepine, and the like. Eight membered heterocycles include, without limitation, azocine, 2H-oxocin, 2H-thiocin, 1,2-diazocine, 2H-1,4-oxazocine, 1,3,4-triazocine, and the like.

Q may also represent a fused heterocyclic ring system such as, for example, indole, benzofuran, benzothiophene, indolizine, isoindole, indoline, benzoxazole, benzisoxazole, benzthiazole, benzisothiazole, benzimidazole, 1H-indazole, quinoline, isoquinoline, quinolizinum, quinazoline, cinnoline, quinoxaline, phthalazine 1,5-naphthyridine, pteridine, 9H-purine, adenine, guanine, and naphthyridine, to name a few. Non-limiting examples of fused heterocyclic ring-systems which are suitable for substituent Q include, but are not limited to:

(i) the following eight membered fused heterocycles:

(ii) the following nine-membered fused heterocycles:

and (iii) the following ten-membered fused heterocycles:

all of which are merely illustrative of the various heterocylic rings which fall within the scope of the invention.

In each of the foregoing heterocyclic ring systems comprising the ring substituents O and/or S, it will be understood that the point of attachment to the ring is other than a sulfur or oxygen atom, by which is meant that Y is either C, CH, or N, rather than O or S. In fused ring systems, the point of attachment may be on either ring, at any suitable position. These rings may be optionally functionalized with one or more groups $R_1$, as defined above, with particular mention being made of halo, hydroxyl, oxo, thiol, $C_{1-4}$ alkyl (e.g., methyl, ethyl, isopropyl, etc.), amino, and dialkylamino. Further, any nitrogen atom may be optionally oxidized to the N-oxide, and any sulfur atom may be optionally oxidized to a sulfoxide.

In a preferred embodiment, Q is a 5 or 6 membered ring comprising, in the ring system, at least one heteroatom other than Y, the heteroatom being selected from oxygen, sulfur, or nitrogen. In another preferred embodiment, Q will comprise an aromatic ring. In various embodiments, Q is a six membered ring selected from pyranyl, pyridyl, pyrazinyl, pyrimidinyl, pyridazinyl, 2H-pyranyl, piperidyl, piperazinyl, morpholinyl, 6H-1,2,5-thiadiazinyl, 2H,6H-1,5,2-dithiazinyl, thiazinyl; 1,2-dithianyl, 1,3-dithianyl, and 1,4-dithianyl; 1,2-dioxanyl, 1,3-dioxanyl, and 1,4-dioxanyl; 1,3,5-triazinyl; or any of the six membered heterocycles provided above, optionally including substitution of groups $R_1$ on the six membered heterocycle. More preferred, the group Q comprises a five membered ring as discussed below.

In one embodiment, the non-proteogenic amino acid of the invention will comprise a 5-membered heterocyclic group, preferably a heteroaryl group, according to formula Ib:

Ib wherein ring Q is further defined by substituents Y, T, U, V, and W;

n is as defined above and is preferably 0 (zero) or 1 so as to define an α-amino acid or a β-amino acid, respectively;

Z is as defined above and preferably represents a single bond or a group $(CH_2)_k$ unit where k is an integer from 1 to 3, preferably from 1 to 2, and more preferred still k is 1; preferably Z is a methylene group —$CH_2$—;

Y is C, CH, or N; and

T, U, V, and W are independently selected from CH, $CR_1$, N, $NR^N$, O, and S, where $R_1$ and $R^N$ are as defined above; and wherein the dotted circle inside the ring indicates that the ring is optionally aromatic or may comprise zero, one, or two double bonds; and in the case where T, U, V, and/or W represent N (nitrogen atom), the nitrogen atom may be optionally oxidized to the N-oxide, and in the case where T, U, V, and/or W represent S (sulfur atom), the sulfur atom may be optionally oxidized to a sulfoxide; and wherein $R_1$ is preferably $C_{1-4}$ alkyl (e.g., methyl, ethyl, etc.), amino, alkylamino, dialkylamino, thiol, hydroxyl, oxo, or halogen.

In one embodiment, Y is C (carbon atom) or N and at least one of T, U, V, and W is N (nitrogen atom). In a preferred embodiment, one pair of adjacent or non-adjacent substituents selected from T, U, V, and W represent CH or $CR_1$, and the other pair independently represents O (oxygen atom), N (nitrogen atom), $NR^N$, or S (sulfur atom); wherein $R_1$ and $R^N$ are as defined above.

In some embodiments, substituents Y, T, U, V, and W will collectively comprise a five membered ring selected from the following: thienyl (2-thienyl or 3-thienyl); furyl (2-furyl or 3-furyl); 2- or 3-oxacyclopentyl; 2- or 3-tetrahydrothiophenyl; 1,2-dithiolanyl; 1,3-dithiolanyl; 2H-pyrrolyl (2H-pyrrol-3-yl, 2H-pyrrol-4-yl, or 2H-pyrrol-5-yl); pyrrolyl (1-pyrrolyl, 2-pyrrolyl or 3-pyrrolyl); imidazolyl (2-imidazolyl, 4-imidazolyl, or 5-imidazolyl); pyrazolyl (1-pyrazolyl, 3-pyrazolyl, 4-pyrazolyl, or 5-pyrazolyl); isothiazolyl (3-isothiazolyl, 4-isothiazolyl, or 5-isothiazolyl); isoxazolyl (3-isoxazolyl, 4-isoxazolyl, or 5-isoxazolyl); 3-furazanyl; pyrrolidinyl (1-pyrrolidinyl, 2-pyrrolidinyl or 3-pyrrolidinyl); pyrrolinyl (1-pyrroline-2-yl, 2-pyrroline-2-yl, 2-pyrroline-3-yl, 2-pyrroline-4-yl, 2-pyrroline-5-yl); imidazolidinyl (1-imidazolidinyl, 2-imidazolidinyl or 4-imidazolidinyl); imidazolinyl (2-imidazolin-2-yl, 2-imidazolin-4-yl, or 2-imidazolin-5-yl); pyrazolidinyl (2-pyrazolidinyl, 3-pyrazolidinyl, or 4-pyrazolidinyl); pyrazolinyl (3-pyrazoline-1-yl, 3-pyrazoline-2-yl, 3-pyrazoline-3-yl, 3-pyrazoline-4-yl, 3-pyrazoline-5-yl); thiazolyl (thiazol-2-yl, thiazol-4-yl, or thiazol-5-yl); oxazolyl (oxazol-2-yl, oxazol-4-yl, oxazol-5-yl); 1,2,3-triazolyl (1,2,3-triazol-1-yl, 1,2,3-triazol-4-yl, or 1,2,3-triazol-5-yl); 1,2,4-triazolyl (1,2,4-triazol-1-yl, 1,2,4-triazol-3-yl, or 1,2,4-triazol-5-yl); isothiazolyl (isothiazol-3-yl, isothiazol-4-yl, or isothiazol-5-yl); 1H-tetrazole (1H-tetrazol-1-yl or 1H-tetrazol-5-yl); and imidizolyl or 1,3-diazolyl (1,3-diazol-1-yl, 1,3-diazol-2-yl, 1,3-diazol-4-yl, 1,3-diazol-5-yl); to name a few, where the species listed in parentheses are representative of the various possible connectivities of these radicals and are not intended to be limiting with regard to the point of attachment. It will be understood that each of the foregoing represent individual embodiments of the invention.

In some embodiments, the amino acids according to the invention will have the structure of formula Ic:

Ic wherein Ω is a heterocyclic ring, preferably a five-membered heterocyclic ring, and preferably selected from the following optionally aromatic rings:

(i)

(ii)

(iii)

(iv)

(v)

wherein $\epsilon_1$, $\epsilon_2$, and $\epsilon_3$, are independently selected from N, NH, $NR^N$, S, and O; with the proviso that where the point of attachment is $\epsilon_1$, $\epsilon_2$, or $\epsilon_3$, that position represents N; and preferably where at least one of $\epsilon_1$, $\epsilon_2$, and $\epsilon_3$, which is not the point of attachment represents N; and wherein the carbon atoms which are not the point of attachment may be optionally substituted with a group $R_1$ as defined above, wherein $R^N$ and $R_1$ are as defined above, $R_1$ preferably being $C_{1-4}$ alkyl (methyl, ethyl, propyl, isopropyl, etc.), amino, alkylamino, dialkylamino, thiol, hydroxyl, $C_{1-4}$ alkoxy (methoxy, ethoxy, etc.), thioalkyl, hydroxyalkyl (e.g., hydroxymethyl, hydroxyethyl, etc.), perfluoromethyl, or halogen (fluorine, chlorine, bromine, iodine). The dashed circles are intended to indicate that each ring is optionally aromatic, but otherwise may comprise zero, one, or two double bonds.

In preferred embodiments according to formula Ic, Ω is selected from:

(i)

(ii)

(iii)

wherein X is either an oxygen atom, $NR^N$, or a sulfur atom; and $R_2$ and $R_3$ are independently selected and may be any group defined above for $R_1$, and preferably represent hydrogen, hydroxyl, halogen (F, Cl, Br, I), $NR^N R^N$, thiol, or $C_{1-4}$ alkyl (preferably methyl); where $R^N$ is defined as above and is preferably hydrogen at each occurrence; and wherein the amino acid may comprise either the R or S enantiomer. In a preferred embodiment, X is sulfur and $R_2$ and $R_3$ are each hydrogen.

More preferred still, the amino acid is an α-amino acid (n=0); Ω is radical (i) listed above; wherein X is sulfur and $R_2$ and $R_3$ each represent hydrogen, thereby defining 4-thiazolylalanine (thiazol-4-ylalanine) having the structure:

In one embodiment, the 4-thiazolylalanine will be either 4-D-thiazolylalanine or 4-L-thiazolylalanine (CAS No. 119433-80-6), with 4-L-thiazolylalanine being preferred. The structure of 4-L-thiazolylalanine is shown below.

4-L-thiazolylalanine

4-L-thiazolylalanine is commercially available from PepTech (Burlington, Mass.) and from Synthetech (Albany, Oreg.). The synthesis of 4-L-thiazolylalanine is described in U.S. Pat. No. 5,275,950 to Dickman et al, the disclosure of which is hereby incorporated by reference herein.

Other non-limiting examples of amino acids contemplated to be suitable in the practice of the invention include proline analogs (L or D) of formula IIa or IIb:

wherein R is as defined above and wherein the amino acid may have either the R or S configuration at the α-carbon.

The non-natural amino acids according to the invention also embrace variants of the naturally occurring amino acids having inverted chirality at the α-carbon, including D-alanine, D-valine, D-leucine, D-isoleucine, D-proline, D-tryptophan, D-phenylalanine, D-methionine, D-serine, D-tyrosine, D-threonine, D-cysteine, D-asparagine, D-glutamine, D-aspartic acid, D-glutamic acid, D-lysine, D-arginine, and D-histidine; or, in the case of isoleucine and threonine, interesting non-natural amino acids are the [R,R], [S,S], [S,R], and [R,S] diastereomers. The non-natural amino acids may also be based on the β analogs of natural amino acids as described in, for example, D. Seebach, et al., Helv. Chim. Acta 1998, 81, 932, D. Seebach, et al., Helv. Chim. Acta 1996, 79, 913, the disclosures of which are hereby incorporated by reference.

As will be evident to one skilled in the art, the amino acids of the invention may be present in zwitterionic form. Further, the invention embraces the use of cosmetically or pharmaceutically acceptable (e.g., non-toxic and/or non-irritating) salts of the amino acids. The salts may be either inorganic or organic acid or base addition salts. Suitable acid salts include but are not limited to acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfate, glucoheptonate, glycerophosphate, hemisulfate, heptonate, hexanoate, fumarate, hydrochloride, hydrobromide, hydroiodide, 2-hydroxyethanesulfate, lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, tosylate, and undecanoate. Special mention may be made of hydrochloride salts. Base addition salts include those formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine, etc. The nitrogen-containing groups, including the amino functional group and nitrogen-containing side chains (e.g., heterocycles), can be quarternized with lower alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl and stearyl chlorides, bromides and iodides, aralkyl halides such as benzyl and phenethyl bromides, to name a few.

The invention also embraces the use of prodrug forms of the amino acids to improve dermal penetration, etc. As used herein, prodrug refers to a compound which is converted in vivo to the amino acid of the invention. The prodrug may be derived from the amino group, the carboxyl group, or both. Suitable prodrug derivatives for modifying these functional groups are well known in the art and described, for example, in Textbook of Drug Design and Discovery, Third Edition (2002), Chapter 14, pp. 411-458, which is hereby incorporated by reference herein.

It is also contemplated that the non-proteogenic aminoacids according to the invention may be functionalized as N-acyl derivatives, including $C_{1-16}$ acyl derivatives, or ester derivatives, including without limitation $C_{1-10}$ alkyl ester derivatives, without limitation, regardless of whether the resulting compound is hydrolyzed in vivo to the free amino acid. In one embodiment, the non-proteogenic aminoacids are provided a $C_{1-16}$ N-acyl derivatives to increase their lipophilicity.

Salts, prodrugs, N-acyl derivatives, and esters are collectively referred to herein as "derivatives" of the free amino acid.

The cosmetic compositions according to the invention can be formulated in a variety of forms for topical application and will comprise from about 0.0001% to about 90% by weight of one or more of the foregoing non-proteogenic amino acids, and preferably will comprise from about 0.0001% to about 20% by weight, more preferably from about 0.001% to about 10% by weight, and most preferably from about 0.001% to about 1%.

The composition can be formulated as a water-in-oil or an oil-in-water emulsion, lotion, cream, serum, spray, stick or other forms suitable for topical application.

The composition may optionally comprise other cosmetic actives and excipients, obvious to those skilled in the art including, but not limited to, fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives, stabilizers, pharmaceutical agents, photostabilizing agents, sunscreens, and mixtures thereof. In addition to the foregoing, the cosmetic compositions of the invention may contain any other compound for the treatment of skin disorders.

The invention also provides a method for treating aging skin by topically applying a composition comprising the inventive composition over the affected area for a period of time sufficient to reduce, ameliorate, dermatological signs of aging. The composition will typically be applied to the skin from 1 to 3 times per 24 hours for as long as is necessary to achieve desired anti-aging results. The treatment regiment may comprise daily application for at least one week, at least two weeks, at least four weeks, at least eight weeks, or at least twelve weeks.

The method includes treatment of skin changes associated with both chronological and intrinsic skin aging. The method is contemplated to be particularly useful for the treatment of UV damaged skin.

The inventive compositions and methods are not typically intended for the treatment of psoriasis, and therefore, in one embodiment, the invention is directed to topical application of one or more of the amino acids described herein, such as 4-L-thiazolylalanine, to skin that is not affected by psoriasis. However, it is within the scope of the invention to topically apply the amino acid compositions to skin affected by psoriasis in order to treat the same area of skin, provided that such skin is also affected by signs of skin aging, e.g., wrinkles, sagging, etc.

EXAMPLES 1.1 Example 1

Stimulation of LOXL1 Activity by L-4 Thiazolylalanine

The enzyme, lysyl oxidase-like 1 ("LOXL1"), has been found to be a key regulator of the renewal of elastin polymer, an extracellular matrix component providing connective tissues, including the skin, with elastic properties. Elastin is not believed to be produced past puberty, after which maintenance of the elastin fiber is the result of competing anti-elastase-elastase activities. As age progresses, an imbalance in the competing activities is noted, resulting in a loss of elasticity in elastin containing tissues. With respect to skin, this loss of elasticity is most commonly observed as wrinkles.

Although the exact mechanisms of renewal/degradation (i.e., antielastase/elastase activity) are unknown, LOXL1 has been identified as an "antielastase" factor, mediating the renewal of elastin fibers by polymerization of tropoelastin monomers (see, e.g., Kagan et al., 2003, *J. Cell. Biochem.*, 88:660-672; and Li et al., 2004, Nat. Genet. 36:178-182, each of which is hereby incorporated by reference in its entirety). Accordingly, agents that act to increase LOXL1 transcription and/or translation or LOXL1 activity are contemplated to increase "antielastase" activity, fostering renewal of elastin fibers and effecting an improvement in elasticity of elastin containing tissues. The ability of L-4 Thiazolylalanine to induce expression of LOXL1 was assayed using a luciferase-reporter system. Addition of L-4 Thiazolylalanine to cultures comprising LOXL1 regulatory elements was found to induce expression of reporter genes significantly over that of controls.

1.1.1 Materials and Methods

Vector construction, transfection and expression: The promoter region of the LOXL1 gene was isolated and cloned into the pGL3 Luciferase reporter plasmid (Promega) by standard methods known in the art and according to manufacturer's instructions. The LOXL1/pGL3 vector and the control vector pRL-NULL (Promega), containing no regulatory elements, were contransfected into the human fibrosarcoma line HT1080 using LipofectAMINE™ LTX Reagent (Invitrogen) according to manufacturer's directions.

Transfected cells were allowed to recover for 24 h. The culture medium was then replaced with fresh medium containing various concentrations of L-4 Thiazolylalanine, and the transfected cells cultured for an additional 24 h.

The cultures were subsequently washed with PBS and exposed to 100 µl cell lysis buffer/25 cm² culture area and gently shaken at room temperature for 30 min. The culture flasks containing the cell lysate were then immediately placed at −80° C.

Determination of Reporter Activity:

The activity of the reporter gene, firefly luciferase, was determined according to the manufacturer's instructions (Dual-Luciferase® Reporter Assay System, Promega). Briefly, the activity of the reporter gene is determined relative to that of a control vector encoding a second luciferase gene, that from *Renilla reniformis*. The relative activities of the genes from test and control cultures are compared for a determination of percent modification of regulatory sequence activity.

1.1.2 Results

Because pGL3 vectors lack the necessary promoter regions to regulate the luciferase gene, the expression of this gene is controlled by the cloned regulatory elements, in this case the regulatory elements of the LOXL1 gene. In triplicate tests, the addition of 1 µg/ml L-4 Thiazolylalanine was found to increase expression of the reporter gene by 57% ($p<0.05$). L-4 Thiazolylalanine is thus indicated as a positive regulator LOXL1 expression, suggesting secondary effects on elastin renewal.

1.2 Example 2

L-4 Thiazolylalanine Inhibition of Inflammatory Pathways

A common symptom of aging skin is the appearance of eczema-like lesions, presenting as areas redness and dry, scaly skin. Although the etiology is unknown, these areas are known to be associated with chronic inflammation. In the past, such lesions were often treated with topical corticosteroids; however, prolonged usage of steroids was found to be associated with many side effects well characterized in the art (e.g., skin atrophy, striae, depigmentation and telangiectasia). In 2000, the FDA approved two new drugs for the topical treatment of eczema, PROTOPIC® (tacrolimus) and ELIDEL® (pimecrolimus), which have since been shown effective in the treatment of multiple inflammatory dermatoses.

Tacrolimus and pimecrolimus are inhibitors of the serine/threonine protease calcineurin, also known as protein phosphatase 2B ("PP2B"). Inhibition of calcineurin blocks dephosphorylation of NFAT (nuclear factor of activated T-cells) preventing production of inflammatory cytokines (see, e.g., Bekersky et al, 2001, J. Am. Acad. Dermatol. 441: S17-S27, hereby incorporated by reference in its entirety). When used topically, calcineurin inhibitors can positively control localized skin irritation.

An ex-vivo phosphatase assay was used to evaluate the ability of L-4 Thiazolylalanine to modulate calcineurin activity. L-4 Thiazolylalanine was found to regulate calcineurin activity in a dose-dependent manner.

1.2.1 Materials and Methods

Ex-vivo phosphatase assay: The modulation of calcineurin activity was monitored using a DiFMUP (6,8-difluoro-7-hydroxy-4-methylcoumarin phosphate) phosphatase assay well characterized in the art (see, e.g., Wegner et al., 2007, Methods Mol. Biol. 365:61-69, hereby incorporated by reference in its entirety). Dephosphorylation of DiFMUP leads to the formation of a highly fluorescent and stable product: Di4MU.

Varying concentrations of L-4 Thiazolylalanine were added to a reaction buffer consisting of 50 mM Tris-HCL, pH 7.4, 0.0125% BSA, 0.1 mM CaCl, 400 U/ml calmodulin and 1 mM NiCl. The L-4 Thiazolylalanine/reaction buffer mixture was incubated at 37° C. for 30 min. DiFMU substrate was then added to a concentration of 10 µM, and the mixture returned to 37° C. incubation for a further 15 min. Fluorescence intensity was determined on a Spectrofluorometer.

1.2.2 Results

At the lowest concentration tested, L-4 Thiazolylalanine was found to slightly enhance calcineurin activity, increasing activity by 6% at a concentration of 0.0001% weight/volume. Increasing L-4 Thiazolylalanine concentration, however, resulted in a dose dependent inhibition of calcineurin activity, decreasing activity by 11% and 63% at 0.001% and 0.01% concentration, respectively. The IC-50 of the compound was estimated as 0.064%. The results suggest that topical application of compositions comprising L-4 Thiazolylalanine will result in improvements of symptoms associated with inflammatory skin conditions.

1.3 Example 3

L-4 Thiazolylalanine Modulation of β1 Integrin Expression

β1 integrin is one component of the transmembrane integrin heterodimer complex, which complex mediates the attachment of cells to extracellular matrix proteins and to other cells. Integrins are able to bind to various components of the extracellular matrix including collagens, laminins and fibronectins, and function in maintaining the structural integrity of skin Reduction in β1 integrin expression has been shown to decrease the elasticity of skin, e.g., in aged and/or sun damaged skin.

A whole cell ELISA assay was used to evaluate the effects of L-4 Thiazolylalanine exposure on β1 integrin expression. L-4 Thiazolylalanine exposure was found to increase β1 integrin expression in human fibroblasts.

1.3.1 Materials and Methods

Cell culture: Human dermal fibroblasts (Cascade Biologics) were cultured in growth medium (DMEM, 5% FBS, 1% L-Glut, and 1% antibiotics) overnight in 60 mm dishes at $3.5 \times 10^5$ cells/ml. Cells were treated with test active or vehicle control diluted in growth medium and incubated for 24 hours at 37° C.

Whole cell ELISA: A B1 integrin kit from Chemicon International was used to assay the expression of B1 integrin on the cell surface following treatment with L-4 thiazolylalanine Medium was aspirated and plates were incubated at 37° C. with Cell Dissociation Buffer (provided with the kit) for 20-25 minutes, cells were centrifuged and resuspended in DMEM without supplements. 100 μl of the cell suspension was added to microtiter plates precoated with a murine anti-human β1 antibody (Chemicon International) that had been blocked for non-specific binding, and the plates incubated at 37° C. for 2 h. Adherent cells were quantitated by a cell staining kit (Chemicon International) according to manufacturer's instructions. Briefly, plates were washed in PBS and adherent cells stained by incubation for 5 min. at room temperature in the kit staining solution. The stained cells were washed in PBS and allowed to air dry for 10 min. Extraction buffer was then added to each well and the plate read at 570 nm on a spectrophotometer.

1.3.2 Results

The percent change in β1 integrin expression was calculated according to the formula:

$$\frac{(\text{mean absorbance of treatment sample}) - (\text{mean absorbance of control sample})}{(\text{mean absorbance of control sample})} \times 100$$

At a concentration of 0.01% (w/v) L-4 Thiazolylalanine, an increase of 225% in the expression of B1 integrin was measured. The results suggest that topical application of compositions comprising L-4 Thiazolylalanine will result in increased expression of β1 integrin, leading to enhanced skin integrity and/or elasticity.

1.4 Example 4

L-4 Thiazolylalanine Modulation of Fibronectin Expression

Fibronectin is a secreted protein that helps form the extracellular matrix regulating the structure and behavior of connective tissues, including the skin Fibronectin mediates the attachment of cells to both other cells (via integrins, see Example 3) and to extracellular matrix components, e.g., collagen, fibrin and heparin. As such, fibronectin is essential for the maintenance of skin integrity, and particularly important in the wound healing process. UV exposure is known to degrade fibronectin in the skin, resulting in decreased expression of the protein in sun-exposed and/or UV damaged areas of the skin. Additionally, fibronectin expression has been found to be decreased in papillary dermis of aging skin.

A competitive inhibition ELISA assay was used to evaluate the effects of L-4 Thiazolylalanine on the expression of fibronectin from normal human adult fibroblasts. L-4 Thiazolylalanine was found to increase expression of fibronectin from fibroblasts in a dose-dependent manner.

1.4.1 Materials and Methods

Cell culture: Human dermal fibroblasts (Cascade Biologics) were cultured in 12-well tissue culture plates in growth medium (DMEM, 5% FBS, 1% L-Glut, and 1% antibiotics) and incubated for 24 hours at 37° C. Cells treated with test active diluted in growth medium and incubated for 72 hours at 37° C., after which conditioned media was collected and assayed for the presence of fibronectin. Fibroblast cultures were then incubated a further 72 hr.

Competitive inhibition ELISA: The presence of fibronectin in the test samples was assayed by a competitive ELISA kit (Chemicon International). Briefly, test and control samples of conditioned media were incubated with a HRP-conjugated, rabbit polyclonal anti-human fibronectin antibody at room temperature for about 10 minutes. The sample/antibody mixture was then transferred to a microtiter plate precoated with a standard amount of human fibronectin that had been blocked for non-specific binding. The plate was incubated for one hour at room temperature, followed by a PBS wash and detection of bound antibody (i.e., detection of bound HRP) by routine methods known in the art. The amount of bound antibody is inversely proportional to the amount of fibronectin in the sample.

1.4.2 Results

The percent change in fibronectin expression due to L-4 Thiazolylalanine treatment was calculated according to the formula:

$$abs\left[\frac{\text{(mean absorbance of treatment sample)} - \text{(mean absorbance of control sample)}}{\text{(mean absorbance of control sample)}}\right] \times 100$$

Increasing concentrations of L-4 Thiazolylalanine resulted in increasing expression and/or production of fibronectin (Table 1):

TABLE 1

| Concentration | Percent Change |
|---|---|
| 0.001% | 36.11% (P < 0.05) |
| 0.0001% | 31.03% (P < 0.05) |
| 0.00001% | 54.34% (P < 0.05) |

The results suggest that topical application of compositions comprising L-4 Thiazolylalanine will result in increased expression of fibronectin, leading to enhanced skin integrity and/or improvements in skin structure.

1.5 Example 5

L-4 Thiazolylalanine Increases Dermal Matrix Molecules In Vivo

In order to ascertain the effect of L-4 thiazolylalanine on collagen levels in human skin in vivo, a test was conducted on about 25 women aged 35-65 years. This human clinical study was approved by an Institutional Review Board and informed consent from the subjects was obtained prior to commencement of the study. The study was conducted in accordance with Title 21 of the Code of Federal Regulations, parts 50 and 56.

A solution of 0.01% L-4 Thiazolylalanine was made up in a vehicle of Propylene glycol:Ethanol:Water at a ratio of 70:20:10. The experimental design of the test was as follows: Thiazolylalanine solution or the vehicle solution without thiazolylalanine was applied to the outer forearm on a 2×2 area of skin (@2 mg/cm2) under a semi-occlusive patch for 24 hours, after which the patch was removed and a fresh patch was applied. This was repeated for 5 days (Monday-Friday), then subjects were rested for the weekend. Patch application was continued in the same manner for the next two weeks, for a total of 15 applications. At the end of the study, 3 mm skin samples were collected by a Board certified Dermatologist, from the area of the patch application, fixed in formalin, embedded in paraffin and processed for histology Skin samples were sectioned and stained with Trichrome stain to visualise collagen fibers and Alcian blue stain to visualize glycosaminoglycans (GAG). The intensity of the collagen and GAG staining was assessed visually under the microscope. A comparison of the samples from the thiazolylalanine treated sites with the vehicle treated site indicated that, in 18/21 (86%) subjects, increased collagen staining was observed in the L4-thiazolylalanine treated sites. 13/21 (62%) subjects treated with L4-thiazolylalanine also showed an increase in GAG staining, relative to skin treated with the vehicle. Increased collagen and GAG in the skin can subsequently lead to improvement in the appearance of signs of aging such as lines, wrinkles, firmness and sagging.

1.6 Example 6

L-4 Thiazolylalanine Induction of Calcitonin Gene Related Peptide (CGRP)

CGRP is the most potent vasodilator currently know, and, as such, is of particular interest for its potential use in aiding wound healing and/or, when used topically, increasing circulation to specific tissues.

A commercially available CGRP Enzyme Immunoassay was used to evaluate the effects of L-4-thiazolylalanine on the expression of CGRP from neuronal cells. L-4-thiazolylalanine was found to induce increased expression of CGRP in in vitro cell culture.

1.6.1 Materials and Methods

Cell culture: PC-12 cells were cultured in FK12 medium supplemented with nerve growth factor according to routine methods known in the art. PC12 cells are derived from a rat pheochromocytoma and terminally differentiate on exposure to nerve growth factor. Once the cells begin to differentiate, they express CGRP. Cultures were incubated in medium containing L-4 Thiazolylalanine for another 24 h. after which conditioned medium was collected and assayed for the presence of CGRP.

CGRP Immunoassay: The presence of CGRP in the test samples was assayed by a sandwich ELISA immunoassay kit. Briefly, test and control samples of conditioned media are mixed with an anti-CGRP antibody conjugated to acetylcholinesterase (the "tracer antibody"), and the mixtures added to plates pre-coated with a monoclonal anti-CGRP antibody (binding to a different epitope of CGRP than the tracer antibody) that had been blocked for non-specific binding. The samples were incubated in the plates and the plates washed and the bound acetylcholinesterase activity determined using Ellman's reagent according to routine methods known in the art. The absorbance of the reagent is directly proportional to the concentration of CGRP in the sample.

1.6.2 Results

The percent change in CGRP expression due to L-4 Thiazolylalanine treatment was calculated according to the formula:

$$\frac{\text{(mean absorbance of treatment sample)} - \text{(mean absorbance of control sample)}}{\text{(mean absorbance of control sample)}} \times 100$$

At a concentration of 0.01% L-4 Thiazolylalanine, the expression of CGRP increased by 69.93% (p<0.05). The results suggest that topical application of compositions comprising L-4 Thiazolylalanine will result in increased expression of CGRP, leading to improvements in skin repair and overall skin condition.

All references including patent applications and publications cited herein are incorporated herein by reference in their entirety and for all purposes to the same extent as if each individual publication or patent or patent application was specifically and individually indicated to be incorporated by reference in its entirety for all purposes. Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

The invention claimed is:

1. A cosmetic composition comprising, in a cosmetically acceptable vehicle, an amount of thiazolylalanine or a derivative thereof effective to enhance LOXL-1 in the skin, in combination with one or more cosmetic actives, wherein said vehicle is in the form of a water-in-oil or oil-in-water emulsion.

2. The cosmetic composition according to claim 1, wherein said thiazolylalanine is L-thiazolylalanine or a derivative thereof.

3. The cosmetic composition according to claim 2, wherein said L-thiazolylalanine is L-4-thiazolylalanine or a derivative thereof.

4. The cosmetic composition according to claim 3, wherein said L-4-thiazolylalanine is in the form of a cosmetically acceptable salt.

5. The cosmetic composition according to claim 1, wherein said one or more cosmetic actives is selected from the group consisting of fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, hormonal compounds, alpha-hydroxy acids, alpha-keto acids, anti-mycobacterial agents, antifungal agents, antimicrobials, antivirals, analgesics, lipidic compounds, anti-allergenic agents, H1 or H2 antihistamines, anti-inflammatory agents, anti-irritants, antineoplastics, immune system boosting agents, immune system suppressing agents, anti-acne agents, anesthetics, antiseptics, insect repellents, skin cooling compounds, skin protectants, skin penetration enhancers, exfollients, lubricants, fragrances, colorants, depigmenting agents, hypopigmenting agents, preservatives, stabilizers, pharmaceutical agents, photo stabilizing agents, and mixtures thereof.

6. The cosmetic composition according to claim 1, wherein said effective amount is between about 0.0001% to about 20% by weight of the total composition.

7. The cosmetic composition according to claim 6, wherein said effective amount is between about 0.001 and about 10% by weight of the total composition.

8. The cosmetic composition according to claim 7, wherein said one or more cosmetic actives is selected from the group consisting of fillers, emulsifying agents, antioxidants, surfactants, film formers, chelating agents, gelling agents, thickeners, emollients, humectants, moisturizers, vitamins, minerals, viscosity and/or rheology modifiers, sunscreens, keratolytics, depigmenting agents, retinoids, alpha-hydroxy acids, alpha-keto acids, anti-inflammatory agents, anti-irritants, anti-acne agents, anesthetics, insect repellents, skin cooling compounds, skin protectants, skin penetration enhancers, exfollients, lubricants, fragrances, colorants, depigmenting agents, hypopigmenting agents, preservatives, stabilizers, photo stabilizing agents, and mixtures thereof.

9. The cosmetic composition according to claim 7, wherein said effective amount is between about 0.001 and about 1% by weight of the total composition.

10. The cosmetic composition according to claim 9, wherein said at least one or more cosmetic actives is selected from the group consisting of antioxidants, film formers, emollients, humectants, moisturizers, vitamins, sunscreens, keratolytics, depigmenting agents, retinoids, hormonal compounds, alpha-hydroxy acids, alpha-keto acids, anti-inflammatory agents, anti-irritants, anti-acne agents, insect repellents, skin cooling compounds, skin protectants, skin penetration enhancers, exfollients, depigmenting agents, hypopigmenting agents, and mixtures thereof.

11. The cosmetic composition according to claim 9, wherein said one or more cosmetic actives is selected from the group consisting of antioxidants, film formers, emollients, humectants, moisturizers, vitamins, sunscreens, keratolytics, depigmenting agents, retinoids, hormonal compounds, alpha-hydroxy acids, alpha-keto acids, anti-inflammatory agents, anti-irritants, anti-acne agents, insect repellents, skin cooling compounds, skin protectants, skin penetration enhancers, exfollients, depigmenting agents, hypopigmenting agents, and mixtures thereof.

* * * * *